(12) United States Patent
Ming et al.

(10) Patent No.: US 12,226,081 B2
(45) Date of Patent: Feb. 18, 2025

(54) CAPSULE ENDOSCOPE

(71) Applicants: ANKON TECHNOLOGIES CO., LTD, Wuhan (CN); ANX IP HOLDING PTE. LTD., Singapore (SG)

(72) Inventors: Fanhua Ming, Wuhan (CN); Bo Feng, Wuhan (CN); Rong Wang, Wuhan (CN); Yun Chen, Wuhan (CN); Xinhong Wang, San Diego, CA (US); Xiaodong Duan, Pleasanton, CA (US); Guohua Xiao, Plano, CA (US)

(73) Assignees: ANKON TECHNOLOGIES CO., LTD., Wuhan (CN); ANX IIP HOLDING PTE. LTD., Singapore (SG)

( * ) Notice: Subject to any disclaimer, the term of this patent is extended or adjusted under 35 U.S.C. 154(b) by 1087 days.

(21) Appl. No.: 17/256,634

(22) PCT Filed: Sep. 18, 2018

(86) PCT No.: PCT/CN2018/106205
§ 371 (c)(1),
(2) Date: Dec. 28, 2020

(87) PCT Pub. No.: WO2020/000687
PCT Pub. Date: Jan. 2, 2020

(65) Prior Publication Data
US 2021/0259531 A1 Aug. 26, 2021

(30) Foreign Application Priority Data
Jun. 28, 2018 (CN) .......................... 201810685479.5

(51) Int. Cl.
*A61B 1/04* (2006.01)
*A61B 1/00* (2006.01)

(52) U.S. Cl.
CPC .......... *A61B 1/041* (2013.01); *A61B 1/00016* (2013.01); *A61B 2562/162* (2013.01);
(Continued)

(58) Field of Classification Search
CPC .... H01Q 1/362; A61B 1/041; A61B 5/07–076
See application file for complete search history.

(56) References Cited

U.S. PATENT DOCUMENTS

2006/0264702 A1* 11/2006 Ishibashi .................. A61B 1/04
600/101
2009/0234203 A1* 9/2009 Arita ...................... A61B 5/073
600/302

(Continued)

FOREIGN PATENT DOCUMENTS

CN 102802499 11/2012
CN 104720806 6/2015
(Continued)

*Primary Examiner* — Alexandra L Newton
(74) *Attorney, Agent, or Firm* — Treasure IP Group, LLC

(57) ABSTRACT

The present invention discloses a capsule endoscope, which comprises an enclosure, and an imaging unit, a data processing unit and an antenna unit arranged in the enclosure. The enclosure comprises a cylindrical middle enclosure and two hemispherical covers connected to both ends of the middle enclosure, and the antenna unit is arranged close to the inner surface of the middle enclosure. The antenna unit is arranged close to the inner surface of the middle enclosure. Such arrangement can save internal space and improve the space utilization, and also, the arrangement of the antenna unit does not affect the layout of the imaging unit.

10 Claims, 2 Drawing Sheets

(52) U.S. Cl.
CPC ... *A61B 2562/164* (2013.01); *A61B 2562/166* (2013.01); *A61B 2562/227* (2013.01)

(56) References Cited

U.S. PATENT DOCUMENTS

| | | | | |
|---|---|---|---|---|
| 2010/0016672 | A1* | 1/2010 | Segawa | A61B 1/041 600/173 |
| 2016/0111775 | A1 | 4/2016 | Yoon et al. | |
| 2017/0346194 | A1* | 11/2017 | Chamberland | H01Q 9/18 |

FOREIGN PATENT DOCUMENTS

| | | |
|---|---|---|
| CN | 204927491 | 12/2015 |
| CN | 107134634 | 9/2017 |
| CN | 107174188 | 9/2017 |
| CN | 107822584 | 3/2018 |
| WO | 2014/193922 | 12/2014 |
| WO | 2018/051328 | 3/2018 |

* cited by examiner

CAPSULE ENDOSCOPE

CROSS-REFERENCE OF RELATED APPLICATIONS

The application claims priority to PCT application PCT/CN2018/106205, filed on Sep. 18, 2018, which in turn takes priority from Chinese Patent Application No. 201810685479.5 filed on Jun. 28, 2018, which is entitled "capsule endoscope", the contents of both the PCT application and Chinese application are incorporated by reference herein.

FIELD OF INVENTION

The present invention relates to a medical device, and more particularly to a capsule endoscope.

BACKGROUND

Capsule endoscope, depending on its high reliability and safety, has become an effective device for the diagnosis of gastrointestinal diseases and has obtained high recognition in international medical device field. A capsule endoscope comprises an imaging unit, a data processing unit, a wireless transmission unit, etc. After ingested into a subject, the capsule endoscope can take images of stomach or intestine while traveling through gastrointestinal tract of the subject, and transmits the images via the wireless transmission unit to an external receiving unit. The images can be displayed on a display device. Based on the displayed images, a physician can make a diagnosis of gastrointestinal diseases for the subject in a state of painless and non-invasive gastrointestinal peristalsis.

Compared with traditional endoscopy, capsule endoscope in the form of wireless transmission provides a better examination experience for the subject, and can present more vivid images of the digestive tract. However, since the wireless capsule endoscope is confined in a small capsule-shaped enclosure, it has strict requirements on the wireless transmission unit. On the premise of effectively enhancing the sensitivity and accuracy of wireless signal reception, the wireless transmission unit is required to have smaller size and more optimized structure, so that it can be integrated into the space-limited capsule enclosure.

Existing capsule endoscopes still have many problems in wireless signal transmission and reception, resulting in incoherent image data and image packet loss. The main reason is unstable wireless signal and inconsistent antenna performance of the capsule endoscope. So, problems such as misdiagnosis and missed diagnosis are prone to occur, which makes it more difficult for the doctor to make a diagnosis of the capsule endoscope.

The prior art relates to a cylindrical antenna. In order to improve antenna performance, two antennas are arranged at one end of the capsule endoscope, which, for one thing, need to take up a large part of the space inside the capsule endoscope, and for another, have unstable performance in the upper and lower space, resulting in data packet loss.

The prior art also relates to another circularly polarized antenna. The antenna is constructed from a metal radiating plate. Compared with the cylindrical antenna, such structure can save a part of space, but the wireless signal is always unstable. In addition, this antenna needs to be placed at the end of the capsule endoscope, so it is not applicable to the capsule endoscope with front and rear dual lenses.

In view of this, it is necessary to provide an improved capsule endoscope to solve the technical problems.

SUMMARY OF THE INVENTION

The present invention discloses a capsule endoscope, which can save the limited space inside the capsule endoscope and improve the utilization of the space of the capsule endoscope.

It is one object of the present invention, to provide a capsule endoscope, which comprises an enclosure and an imaging unit, a data processing unit and an antenna unit arranged in the enclosure, wherein the enclosure comprises a cylindrical middle enclosure and two hemispherical covers connected to both ends of the middle enclosure, and the antenna unit is arranged close to the inner surface of the middle enclosure.

In an embodiment, the antenna unit comprises a flexible substrate and an antenna disposed on the flexible substrate, and the antenna surrounds and extends spirally along the axis of the middle enclosure.

In an embodiment, the antenna comprises a first end and a second end disposed opposite to each other, wherein the first end and the second end are respectively disposed on two ends having a maximum distance on the flexible substrate.

In an embodiment, a straight line joining the first end and the second end of the antenna is parallel to the axial direction of the middle enclosure.

In an embodiment, when the antenna unit is in an expanded state, the antenna is linearly arranged on the flexible substrate.

In an embodiment, a first junction zone and a second junction zone are formed between the middle enclosure and the two covers respectively, and the flexible substrate comprises a first end portion and a second end portion disposed opposite to each other, wherein the first end portion is disposed in the first junction zone, and the second end portion is disposed in the second junction zone.

In an embodiment, the flexible substrate further comprises a connecting portion connecting the first end portion and the second end portion, and when the flexible substrate is in an expanded state, the first end portion, the connecting portion and the second end portion are connected in a "Z" shape.

In an embodiment, the antenna comprises a first end and a second end disposed opposite to each other and a connecting part connecting the first end and the second end, the first end is on the first end portion, the second end is on the second end portion, and the connecting part passes through the connecting portion.

In an embodiment, the capsule endoscope further comprises a first circuit board arranged in the first junction zone and a second circuit board arranged in the second junction zone, and a flexible circuit board connecting the first circuit board and the second circuit board, the imaging unit comprises a first camera and a second camera respectively arranged in the two covers and respectively connected to the first circuit board and the second circuit board, and the antenna is electrically connected to the first circuit board and/or the second circuit board.

In an embodiment, the length of the antenna ranges from 30 mm to 32 mm.

In an embodiment, the width of the antenna ranges from 0.1 mm to 2 mm.

According to all aspects of the present invention, the antenna unit of the capsule endoscope is arranged close to the inner surface of the middle enclosure. Such arrangement can save the limited space inside the capsule endoscope and improve the internal space utilization of the capsule endoscope, and also, the arrangement of the antenna unit does not affect the layout of the imaging unit, thus ensuring a high applicability.

DETAILED DESCRIPTION

Figure 1:
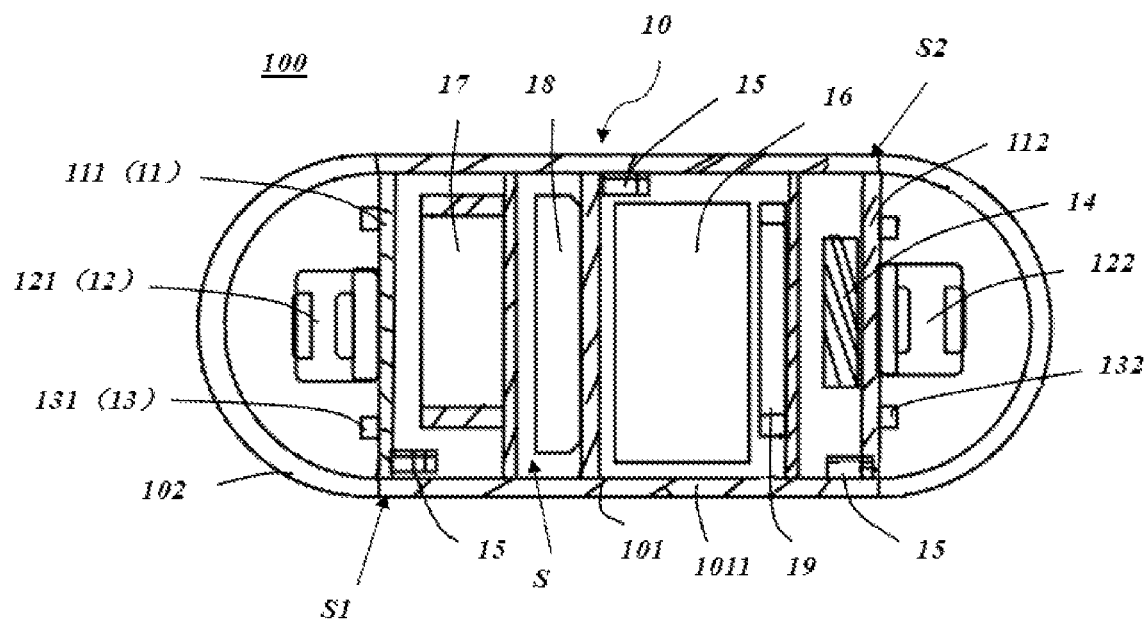
FIG. 1 is a cross-sectional view of a capsule endoscope according to a first embodiment of the present invention.

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

In the figures of the present invention, some sizes of a structure or portion may be exaggerated relative to other structures or portions for ease of illustration, and thus, are merely used to illustrate the basic structure of the subject matter of the present invention.

In addition, the terms representing spatial relative position such as "on", "above", "under", "below", and the like are used herein for ease of illustration to describe the positional relationship of one unit or feature to another unit or feature as shown in the drawings. These terms may be intended to include different orientations of the device in use or operation other than the orientations shown in the figures. For example, if the device shown in the figures is turned over, the units or features that are described as "below" or "under" other units or features can be "above" other units or features. Thus, the exemplary term "below" can encompass two orientations of "below" and "above". The device may be oriented (rotated 90 degrees or other orientations) in other ways and the space related descriptors used herein are interpreted accordingly.

Referring to FIG. 1, a cross-sectional view of a capsule endoscope 100 according to a first embodiment of the present invention.

The capsule endoscope 100 comprises an enclosure 10 and a circuit board assembly 11, an imaging unit 12, an illumination unit 13, a radio frequency transmission unit 14, an antenna unit 15, a permanent magnet 16, a motion sensor 17, a battery 18, and a data processing unit 19. The circuit board assembly 11, the imaging unit 12, the illumination unit 13, the radio frequency transmission unit 14, the antenna unit 15, the permanent magnet 16, the motion sensor 17, the battery 18, and the data processing unit 19 are arranged in the enclosure 10.

The enclosure 10 comprises a cylindrical middle enclosure 101 and two hemispherical covers 102 connected to both ends of the middle enclosure 101.

Herein, the middle enclosure 101 is opaque, the cover 102 is transparent, the middle enclosure 101 and the cover 102 can be molded separately and then assembled together, but not limited to this.

It should be noted that the enclosure 10 is not limited to a capsule shape as shown in the FIG. 1, but may be in the shape of an American football or other shapes.

A first junction zone S1 and a second junction zone S2 are formed between the middle enclosure 101 and the two covers 102, respectively.

The circuit board assembly 11 comprises a first circuit board 111 arranged in the first junction zone S1 and a second circuit board 112 arranged in the second junction zone S2.

Herein, both of the first circuit board 111 and the second circuit board 112 are a printed circuit board (PCB), and the circuit board assembly 11 further comprises a flexible circuit board (not shown) electrically connected to the first circuit board 111 and the second circuit board 112. Thus, the first circuit board 111 and the second circuit board 112 can be bent opposite the flexible circuit board to be arranged in the first junction zone S1 and the second junction zone S2, respectively.

The first circuit board 111 and the second circuit board 112 can be a circular circuit board, and the flexible circuit board can be arranged close to the inner surface 1011 of the middle enclosure 101 to reduce the space occupied by the circuit board assembly 11.

It should be noted that the first circuit board 111 and the second circuit board 112 can be independent circuit boards or comprise a plurality of circuit boards. For example, according to the layout and requirements of the internal components of the capsule endoscope 100, the first circuit board 111 comprises a plurality of small circuit boards, and the plurality of small circuit boards are electrically connected through a flexible circuit board.

The imaging unit 12 comprises a first camera 121 and a second camera 122 that are arranged in the two covers 102 respectively.

The first camera 121 is connected to the side of the first circuit board 111 away from the second circuit board 112, and the second camera 122 is connected to the side of the second circuit board 112 away from the first circuit board 111. The first camera 121 and the second camera 122 can be a traditional CMOS image sensor.

The illumination unit 13 comprises a first illumination group 131 arranged around the first camera 121 and a second illumination group 132 arranged around the second camera 122. The first illumination group 131 and the second illumination group 132 can respectively comprise a plurality of LEDs which are evenly distributed around the corresponding cameras.

The radio frequency transmission unit 14, the antenna unit 15, the permanent magnet 16, the motion sensor 17, the battery 18, and the data processing unit 19 are all arranged in the accommodating space S surrounded by the middle enclosure 101. The radio frequency transmission unit 14, the antenna unit 15, the permanent magnet 16, the motion sensor 17, the battery 18 and the data processing unit 19 are all electrically connected to the circuit board assembly 11 to realize the interaction of signals.

The radio frequency transmission unit 14 and the antenna unit 15 combine to form a wireless communication module.

The radio frequency transmission unit 14 is disposed on the side of the second circuit board 112 close to the first circuit board 111, and the radio frequency transmission unit 14 is electrically connected to the second circuit board 112 and the antenna unit 15.

The radio frequency transmission unit 14 is used to convert radio frequency signals into electrical signals.

The antenna unit 15 is arranged close to the inner surface 1011 of the middle enclosure 101.

Herein, the antenna unit 15 is a sheet structure, and "close to" means that one side of the antenna unit 15 is adjacent to or directly in contact with the inner surface 1011 of the middle enclosure 101. The antenna unit 15 can be fixed to the inner surface 1011 by adhesive to improve the stability of the position of the antenna unit 15, and facilitate the assembly of the antenna unit 15.

The permanent magnet 16 is used to cooperate with an external control device (not shown). The external control device can control the capsule endoscope 100 to actively move inside a subject via the permanent magnet 16.

The motion sensor 17 is used to obtain the position and orientation of the capsule endoscope 100, and the motion sensor 17 can convert non-electric (such as velocity, pressure) changes into electric changes, thereby facilitating active control of the motion of the capsule endoscope 100.

The battery 18 is used to supply power to other components of the capsule endoscope 100.

The data processing unit 19 is used to compress, convert, and analyze the data of the imaging unit 12, the radio frequency transmission unit 14, the illumination unit 13, the motion sensor 17, etc.

In addition, the data processing unit 19 can also generate an illumination control signal to control the illumination intensity of the illumination unit 13, and the data processing unit 19 can achieve data communication with an external host through the radio frequency transmission unit 14.

In the embodiment, the antenna unit 15 of the capsule endoscope 100 is arranged close to the inner surface 1011 of the middle enclosure 101. Such arrangement can save the limited space inside the capsule endoscope 100 and improve the internal space utilization, and also, the arrangement of the antenna unit 15 does not affect the layout of the imaging unit 12, thus ensuring a high applicability. The antenna unit 15 of the embodiment is suitable for a wireless capsule endoscope with a front and rear dual camera structure.

Figure 2:
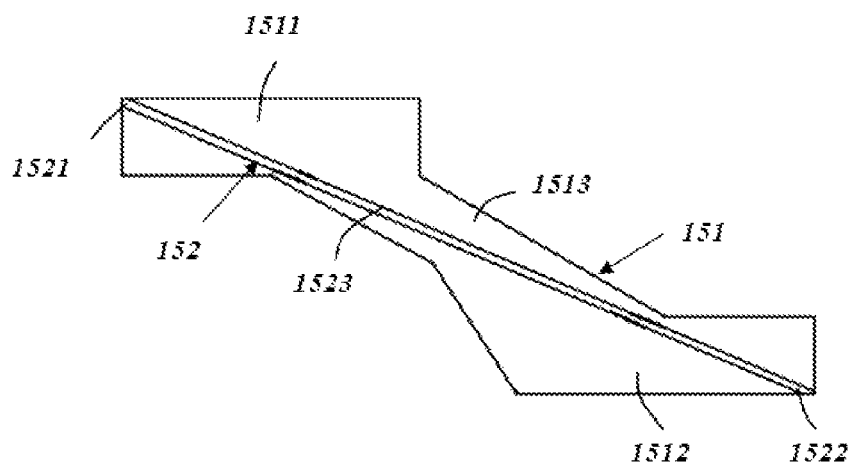
FIG. 2 is a schematic diagram of an antenna unit of the first embodiment of the present invention in an expanded state.
Figure 3:
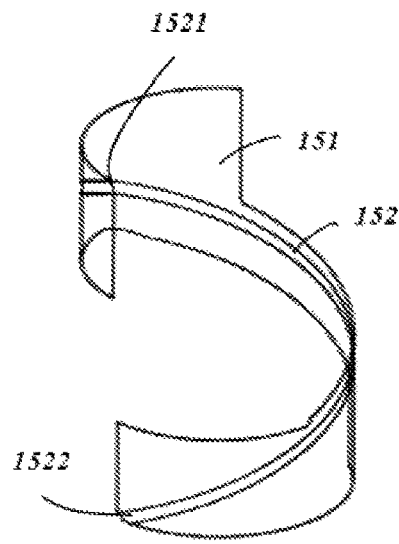
FIG. 3 is a schematic diagram of the antenna unit of the first embodiment of the present invention in a wound state.

Referring to FIG. 2 and FIG. 3, the antenna unit 15 comprises a flexible substrate 151 and an antenna 152 disposed on the flexible substrate 151. The antenna 152 surrounds and extends spirally along the axis of the middle enclosure 101.

Herein, the antenna 152 is a copper wire, the flexible substrate 151 is, for example, a flexible polyester film, and the antenna unit 15 is formed by welding the copper wire to the polyester film.

The diameter of the copper wire ranges from 0.1 mm-2 mm.

In the embodiment, the antenna unit 15 has the advantages of small size, light weight, flexibility, etc., which allow the antenna unit 15 to be disposed inside the capsule endoscope 100.

In addition, the antenna unit 15 is arranged on the inner surface 1011 of the middle enclosure 101, so that the antenna 152 can be disposed in a spirally wound state. In this way, the spatial length of the antenna 152 can be increased, and thereby the radiation performance of the antenna 152 can be improved.

One end of the antenna 152 is electrically connected to the first circuit board 111 and/or the second circuit board 112, for example, by welding.

Specifically, the flexible substrate 151 comprises a first end portion 1511 and a second end portion 1512 that are disposed opposite to each other, and a connecting portion 1513 that connects the first end portion 1511 and the second end portion 1512.

The first end portion 1511 is disposed in the first junction zone S1, and the second end portion 1512 is disposed in the second portion zone S2.

The antenna 152 comprises a first end 1521 and a second end 1522 that are disposed opposite to each other, and a connecting part 1523 that connects the first end 1521 and the second end 1522.

The first end 1521 is on the first end portion 1511 of the flexible substrate 151, the second end 1522 is on the second end portion 1512, and the connecting part 1523 passes through the connecting portion 1513.

Herein, the first end 1521 and the second end 1522 are respectively disposed on two ends having a maximum distance on the flexible substrate 151.

Referring to FIG. 2, it can be understood that the distance between the diagonal corners of the flexible substrate 151 is the maximum, and in this case, the first end 1521 and the second end 1522 are respectively located at two diagonal corners of the flexible substrate 151, so, the spatial length of the antenna 152 can be further increased.

When the antenna unit 15 is in an expanded state, the antenna 152 is linearly arranged on the flexible substrate 151.

Herein, the antenna 152 is a copper wire, as an example, that is, the antenna 152 is a monopole antenna, but it is not limited to this.

It should be noted that "linearly" can refer to a straight line, a curved line, a broken line, etc.

For example, due to the effect of size, frequency range or other internal design factors of the capsule endoscope 100, when the antenna 152 arranged in a "straight line" cannot meet the layout, an arrangement in a "curved line" or "broken line" can be considered.

Specifically, assuming that the 868-915 MHz frequency band is used, the antenna 152 needs a longer length. Without changing the design of other parts of the antenna unit 15, the antenna 152 can be designed in a "curved line" or "broken line" form, so that the antenna 152 can extend in a limited space.

Referring to FIG. 3, when the antenna unit 15 is in a wound state, the straight line joining the first end 1521 and the second end 1522 of the antenna 152 is parallel to the axis of the middle enclosure 101.

In other words, at this time, the projection of the antenna 152 on the radial plane of the middle enclosure 101 is a complete circle.

Below, several specific examples of the antenna unit 15 in the embodiment are described.

Referring to FIG. 2 and FIG. 3, in the first example, when the flexible substrate 151 is in an expanded state, the first end portion 1511, the connecting portion 1513, and the second end portion 1512 are connected in a "Z" shape, and the antenna 152 is arranged diagonally.

The first end portion 1511 and the second end portion 1512 are approximately rectangular. The length of the first end portion 1511 is approximately equal to half of the circumference of the middle enclosure 101, and the length of the second end portion 1512 is also approximately equal to half of the circumference of the middle enclosure 101. When the antenna unit 15 is in a wound state, the first end portion 1511 only occupies the space at one side of the first junction zone S1 (for example, the left space), and the second end portion 1512 only occupies the space at one side of the second junction zone S2 (for example, the right space), and the space occupied by the first end portion 1511 and the second end portion 1512 are on opposite sides, which can further improve the stability of the antenna unit 15 fixed to the inner surface 1011 of the middle enclosure 101, and make the internal structure of the capsule endoscope 100 more compact to avoid increasing the diameter of the capsule endoscope 100.

In addition, the first end portion 1511 and the second end portion 1512 can be fixed to the inner surface 1011 by adhesive, and the connecting portion 1513 can also be fixed to the inner surface 1011 by adhesive.

The advantages of this design are as follows: first, the first end portion 1511 and the second end portion 1512 of the flexible substrate 151 are roughly rectangular, so the contact area between the first end portion 1511, the second end portion 1512 and the inner surface 1011 of the middle enclosure 101 is large, which can improve the stability of combination of the antenna unit 15 and the inner surface 1011; second, the periphery of the connecting portion 1513 is a hollowed out area, which on the basis of ensuring that the flexible substrate 151 can carry the antenna 152 and minimize the area of the antenna unit 15, thereby saving the internal space of the capsule endoscope 100 and making the internal structure of the capsule endoscope 100 more compact; third, saving materials and effectively reducing cost; fourth, simple assembly, even if the antenna unit 15 has a certain deviation in size, it can be easily assembled into the middle enclosure 101; fifth, the antenna unit 15 can effectively avoid the flexible circuit board.

Figure 4:
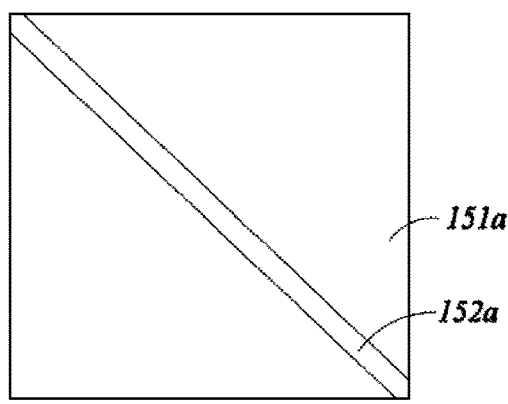
FIG. 4 is a schematic diagram of the antenna unit of a second embodiment of the present invention in an expanded state.

Referring to FIG. 4, in a second embodiment of the present invention, when the flexible substrate 151a is in an expanded state, the flexible substrate 151a is rectangular in its entirety, and the antenna 152a is arranged diagonally.

Figure 5:
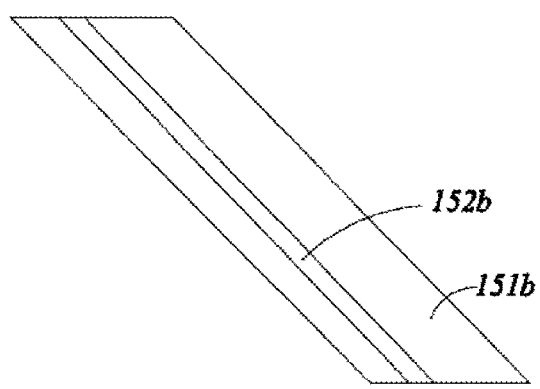
FIG. 5 is a schematic diagram of the antenna unit of a third embodiment of the present invention in an expanded state.

Referring to FIG. 5, in a third embodiment of the present invention, when the flexible substrate 151b is in an expanded state, the flexible substrate 151b is a parallelogram in its entirety, and the antenna 152b is arranged parallel to the long side of the parallelogram.

In the embodiment, in order to make the capsule endoscope 100 work in the 2.4 GHz civil frequency band, the length of the antenna 152 ranges from 30 mm to 32 mm.

Preferably, the length of the antenna 152 is 31 mm.

Herein, the length of the antenna 152 can be adjusted according to the frequency band requirements.

The width of the antenna 152 ranges from 0.1 mm to 2 mm.

Configuration principles of the antenna 152 comprises: (1) the length of the antenna 152 matches the size of the capsule endoscope 100; (2) the internal space of the capsule endoscope 100 is saved as much as possible.

In addition, the calculation formula for the length of the antenna 152 is:

$$L = \frac{c}{f} \times \frac{1}{4}.$$

where, c is the speed of light, and f is the operating frequency of the antenna 152.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The series of detailed descriptions listed above are only specific descriptions of feasible implementations of the present invention, and are not intended to limit the protection scope of the present invention. On the contrary, any equivalent implementations made without departing from the technical spirit of the present invention, the modifications and variations are possible within the scope of the appended claims.

What is claimed is:

1. A capsule endoscope, comprising:
an enclosure;
an imaging unit, a data processing unit and an antenna unit that are arranged in the enclosure;
wherein the enclosure comprises a cylindrical middle enclosure and two hemispherical covers connected to both ends of the middle enclosure, and the antenna unit is arranged close to the inner surface of the middle enclosure,
wherein a length of the antenna unit matches a size of the capsule endoscope;
the length of the antenna unit (L) is determined by $$L = \frac{c}{f} \times \frac{1}{4}$$

wherein, c is a speed of light, and f is an operating frequency of the antenna unit;
the antenna unit comprises a flexible substrate and an antenna disposed on the flexible substrate, and the antenna surrounds and extends spirally along the axis of the middle enclosure;
the flexible substrate comprises a first end portion and a second end portion disposed opposite to each other,
the first end portion and the second end portion are rectangular;
a length of the first end portion is equal to half of a circumference of the middle enclosure, and
a length of the second end portion is also equal to half of the circumference of the middle enclosure;
when the antenna unit is in a wound state, the first end portion only occupies a space at one side of a first junction zone S1 and the second end portion only occupies the space at one side of a second junction zone S2, and the space occupied by the first end portion and the second end portion are on opposite sides, configured to improve stability of the antenna unit fixed to the inner surface of the middle enclosure, and make internal structure of the capsule endoscope more compact to avoid increasing the diameter of the capsule endoscope.

2. The capsule endoscope of claim 1, wherein the antenna comprises a first end and a second end disposed opposite to each other, wherein the first end and the second end are respectively disposed on two ends having a maximum distance on the flexible substrate.

3. The capsule endoscope of claim 2, wherein a straight line joining the first end and the second end of the antenna is parallel to the axial direction of the middle enclosure.

4. The capsule endoscope of claim 1, wherein when the antenna unit is in an expanded state, the antenna is linearly arranged on the flexible substrate.

5. The capsule endoscope of claim 1, wherein
the first junction zone and the second junction zone are formed between the middle enclosure and the two covers respectively and the first end portion is disposed in the first junction zone, and the second end portion is disposed in the second junction zone.

6. The capsule endoscope of claim 5, wherein the flexible substrate further comprises a connecting portion connecting the first end portion and the second end portion, and when the flexible substrate is in an expanded state, the first end portion, the connecting portion and the second end portion are connected in a "Z" shape.

7. The capsule endoscope of claim 6, wherein the antenna comprises a first end and a second end disposed opposite to each other and a connecting part connecting the first end and the second end, wherein the first end is on the first end portion, the second end is on the second end portion, and the connecting part passes through the connecting portion.

8. The capsule endoscope of claim 5, wherein the capsule endoscope further comprises a first circuit board arranged in the first junction zone and a second circuit board arranged in the second junction zone, and a flexible circuit board connecting the first circuit board and the second circuit board, the imaging unit comprises a first camera and a second camera respectively arranged in the two covers and respectively connected to the first circuit board and the second circuit board, and the antenna is electrically connected to the first circuit board and/or the second circuit board.

9. The capsule endoscope of claim 1, wherein the length of the antenna ranges from 30 mm to 32 mm.

10. The capsule endoscope of claim 1, wherein the width of the antenna ranges from 0.1 mm to 2 mm.

* * * * *